ns in the presence of catalysts and of organic compounds which absorb light of from 2000 to 8000 A and which are irradiated with such light. The compounds which can be prepared by the process of the invention are valuable starting materials for the production of dyes and pest control agents.

United States Patent [19]

Fischer et al.

[11] B 4,012,305
[45] Mar. 15, 1977

[54] PRODUCTION OF 1-METHYL-3-PHENYLINDANS

[75] Inventors: Martin Fischer, Ellerstadt; Hans-Juergen Quadbeck-Seeger, Ludwigshafen; Gerhard Kilpper, Mannheim; Hans-Georg Schecker, Ludwigshafen; Waldemar Koehler, Frankenthal, all of Germany

[73] Assignee: Badische Anilin- & Soda-Fabrik Aktiengesellschaft, Ludwigshafen (Rhine), Germany

[22] Filed: Apr. 25, 1973

[21] Appl. No.: 354,222

[44] Published under the second Trial Voluntary Protest Program on March 23, 1976 as document No. B 354,222.

[30] Foreign Application Priority Data

May 6, 1972 Germany .......................... 2222368

[52] U.S. Cl. .......................................... 204/162 R
[51] Int. Cl.² .......................................... C07C 3/24
[58] Field of Search ................................ 204/162 R

[56] References Cited

UNITED STATES PATENTS 3,483,102  12/1969  Arnold et al. ............. 204/162 R X

FOREIGN PATENTS OR APPLICATIONS 768,410  2/1971  Belgium

*Primary Examiner*—Leland A. Sebastian
*Attorney, Agent, or Firm*—Johnston, Keil, Thompson & Shurtleff

[57] ABSTRACT

A process for the production of 1-methyl-3-phenylindans by dimerization of styrenes in the presence of catalysts and of organic compounds which absorb light of from 2000 to 8000 A and which are irradiated with such light. The compounds which can be prepared by the process of the invention are valuable starting materials for the production of dyes and pest control agents.

13 Claims, No Drawings

PRODUCTION OF 1-METHYL-3-PHENYLINDANS

The invention relates to a process for the production of 1-methyl-3-phenylindans by dimerization of styrenes in the presence of catalysts and oxidizing agents.

It is known that in the presence of phosphoric acid, sulfuric acid or other mineral acids and in the presence of solid acid catalysts at elevated temperatures styrene can be dimerized into a mixture of 1,3-diphenylbutene-(1) and 1-methyl-3-phenylindan (J. Org. Chem., volume 19 (1954), pages 17 et seq. and volume 27 (1962), pages 1636 et seq.; J. Chem. Soc., 1964, pages 1573 et seq.; Organic Synthesis, Coll. volume IV (J. Wiley, N.Y.), pages 665 et seq.). The reaction is a complicated system of side reactions and secondary reactions. The first stage in the reaction is the dimerization of monomeric styrene into 1,3-diphenylbutene-(1). Cyclization of the trans-form into the indan follows as a secondary reaction. Starting from the cis-form and the trans-form trimers and other polymers of styrene are formed as further undesirable byproducts.

None of these methods is satisfactory economically on an industrial scale. While at high reaction velocities (space-time yields of about 1 kg of indan per liter of reaction volume per hour) only yields of end products of up to 30% of theory together with large amounts of higher linear styrene oligomers are obtained, higher yields are obtained at lower reaction velocities but only small space-time yields of about 0.01 kg per liter per hour. It is known from Belgian Patent Specifications Nos. 757,175 and 759,536 that styrenes are dimerized into 1-methyl-3-phenylindans in the presence of phosphoric acid, sulfuric acid and/or haloalkanoic acids. The reaction is carried out at a temperature above 150°C or a mixture of styrene and the indane to be produced is used, instead of styrene, as the starting material at a temperature lower than 150°C. In the latter case the concentration of end product in the starting mixture is higher than the concentration of styrene. The two methods are only carried out continuously.

It is known from Belgian Patent Specification No. 768,410 that styrenes are dimerized into 1-methyl-3-phenylindans in the presence of acids and polymerization inhibitors. The process is unsatisfactory in the yield of pure end product, depending on the polymerization inhibitor used, and because some of the additives are very expensive.

The object of this invention is to provide a new process for producing 1-methyl-3-phenylindans in a simpler manner with good yields and better space-time yields and in good purity.

We have found that 1-methyl-3-phenylindans of the general formula:

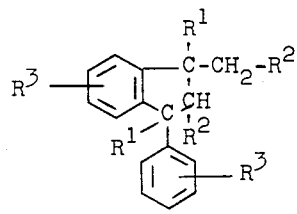

(I)

in which $R^1$, $R^2$ and $R^3$ may be identical or different and each denotes alkyl or hydrogen and $R^3$ may also denote halogen are advantageously obtained by dimerization of a styrene in the presence of a catalyst, when the reaction with a styrene of the general formula:

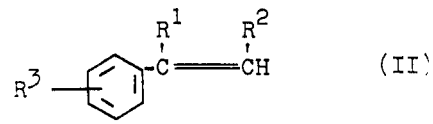

(II)

in which $R^1$, $R^2$ and $R^3$ have the meanings given above is carried out in the presence or absence of an oxidizing agent and in the presence of an organic compound which absorbs light of from 2000 to 8000 A and has been irradiated with such light.

When styrene is used, the reaction may be represented by the following equation:

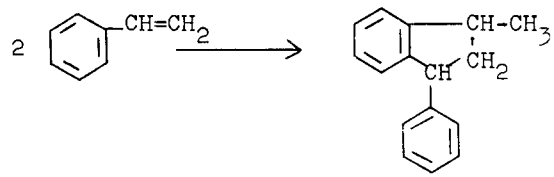

The process according to the invention gives 1-methyl-3-phenylindans in better yields or space-time yields and in good purity by a simpler and more economical method than the prior art methods. High yields of end product can be achieved at good space-time yields.

These advantageous results are achieved in continuous operation at temperatures below 150°C and without mixing end product with the initial styrene. In contrast to the said first two Belgian Patent Specifications referred to the process may also be carried out batchwise and this is of economic significance for processing small batches or residues of starting material. The process according to the present invention gives a better yield of end product than that of Belgian Patent Specification No. 768,410. These advantageous results are surprising having regard to the teaching that light (in the presence or absence of sensitizers) initiates, promotes and accelerates the polymerization of styrene into polymerized styrenes (Houben-Weyl, "Methoden der organischen Chemie," volume XIV/1, page 769).

Preferred starting materials of the general formula (II) and consequently preferred end products (I) are those in whose formulae $R^1$, $R^2$ and $R^3$ are identical or different and each denotes alkyl of one to four carbon atoms or hydrogen and $R^3$ may also denote chlorine or bromine. The following are examples of suitable starting materials: styrene, o-chlorostyrene, p-bromostyrene, p-methylstyrene, α-methylstyrene, β-propylstyrene, α,β-dimethylstyrene and α-isobutylstyrene. The starting materials may be used in gaseous or liquid form.

The catalysts may be any of the catalysts suitable for the polymerization of styrene, for example an acid and/or a silicic acid compound. The acids used as a rule are phosphoric acid, sulfuric acid and/or haloalkanoic acids, in the case of a gaseous starting material (II) advantageously in a ratio of 50 to 1000, particularly of 100 to 500, moles of acid (calculated as 100%) per mole of starting material (II). In the case of liquid starting materials (II), 4 to 0.25, particularly 2 to 0.5, parts by volume of acid (calculated as 100%) is used per part by volume of starting material (II). The acids may be used in concentrated form or mixed with water. The following are examples: metaphosphoric acid, pyrophosphoric acid or particularly orthophosphoric acid, advantageously in aqueous solution, with 50 to 90%, preferably with 60 to 80%, by weight of phosphorus pentoxide; aqueous 50 to 80% by weight sulfuric acid; monochloroacetic acid, dichloroacetic acid, trichloroacetic acid and chloropropionic acid. Mixtures of these acids, advantageously of phosphoric acid and sulfuric acid with or without water, preferably in a weight ratio of 70 to 95% by weight of phosphoric acid (calculated as 100%), 0 to 20% by weight of sulfuric acid (calculated as 100%) and 0 to 20% by weight of water, may also be used.

The silicic acid compounds used are advantageously silicates, for example sodium aluminum silicate, calcium aluminum silicate, bleaching clays, fuller's earth, clays, kaolin, allophanes, zeolites, montmorillonite, pumice, Florida earth, asbestos, mullite, bentonite; silicic acid, silica gel or kieselguhr. The silicic acid compound may also contain metal oxide, for example aluminum, zirconium or magnesium oxide.

Suitable solid phosphoric acid catalysts include metaphosphoric, pyrophosphoric and/or preferably orthophosphoric acid which may conveniently be used as such or in the form of an aqueous solution applied to a carrier. The phosphoric acid may also be in the form of a polyphosphoric acid, for example with 72 to 88% by weight of $P_2O_5$. The carrier may advantageously be one of the said silicic acid compounds, preferably precipitated silicic acid, silica gel or kieselguhr, but bauxite, magnesite, aluminum oxide, activated carbon and quartz may also be used as carrier. The phosphoric acid catalysts contain the phosphoric acid (calculated as orthophosphoric acid irrespective of the actual constitution) generally in an amount of 10 to 80%, preferably 30 to 80%, by weight of acid based on the carrier material. The production of these catalysts is carried out by conventional methods, for example by applying the acid to a carrier, drying and calcination, for example at from 200° to 900°C in a reducing, oxidizing or inert atmosphere.

The particle size of the solid catalysts is preferably from 1 to 10 millimeters. It may have any shape, for example spherical or granular. The solid catalyst is generally used in an amount of from 10 to 1000%, preferably from 80 to 200%, by weight based on the amount of starting material (II) supplied to the reaction per hour. As regards the preparation of the catalysts, reference is made to Houben-Weyl, "Methoden der organischen Chemie", volume 4/2, pages 142 et seq., and Ullmanns "Encyklopadie der technischen Chemie", volume 9, pages 271 et seq.

The invention is based on the observation that organic compounds absorbing light of 2000 to 8000 A are activated in a quite specific manner by irradiation with such light and surprisingly promote the dimerization and at the same time the cyclization of styrenes to the corresponding indans. The compounds capable of being activated by light may be gaseous, solid or liquid. The organic compounds are advantageously polymerization inhibitors as well. Light-absorbing substances which prevent or strongly retard the polymerization of monomers and thus act as stabilizers in relation to the monomers may advantageously be used as organic compounds. Those are preferred which inhibit the polymerization of vinyl compounds. Light-absorbing organic compounds, for example nitrobenzene, and additionally polymerization inhibitors, for example phenylthiourea, may also be used, if desired together with oxidizing agents.

It is advantageous to use the following organic compounds: thioureas, for example thiourea, methylthiourea, phenylthiourea, N,N-diphenylthiourea, N,N'-diphenylthiourea, N-methyl-N-(p-toluyl) -thiourea, S-benzyl-N-phenylisothiouronium picrate, S-methyldithiobiuret hydrochloride, phenylmethylthiourea, 2,4-dimethoxyphenylthiourea, 4-methoxyphenylthiourea, di-n-butylthiourea, 1-benzoylthiosemicarbazide, dithiobiuret; phenols, thiophenols and their ethers, for example hydroquinone monomethyl ether, 4-tertiary -butylpyrocatechol, N-benzyl-p-aminophenol, o-aminophenol; sulphur-containing heterocyclic compounds having sulphur as a substituent or in a side chain on the heterocyclic ring, for example 2-mercaptobenzoimidazole, 2-mercapto-4-anilinoquinazoline, 2-thiocyanomethylbenzimidazole, or having a sulpher atom in the heterocyclic ring, for example phenothiazine, thionaphthene, 2-mercaptobenzothiazole, 2-aminobenzothiazole, 3-aminobenzoisothiazole, 2-methylbenzothiazole, diphenylene sulphide, 2,5-dimercapto-1,3,4-thiadiazole, thianthrene, leucomethylene blue, tetramethylenetrithione; substituted aromatic amines, for example diphenylamine, m-acetoaminodiphenylamine, N-phenyl-$\alpha$-naphthylamine, N-phenyl-$\beta$-naphthylamine, p-isopropylaminodiphenylamine; aromatic hydrazines, for example hydrazobenzene; nitroso compounds, for example o-nitrosophenol, m-nitrosophenol, p-nitrosophenol, cupferron (ammonium nitroso-$\beta$-phenylhydroxylamine), nitrogen monoxide, dinitrogen tetroxide; organic phosphorus compounds, for example triphenyl phosphine, triphenyl phosphite; thioamides, for example thioacetamide, anthranilic thioamide, 2-amino-5-nitrothiobenzamide, 2-amino-3-bromo 5-nitrothiobenzamide, 2-amino-3,5-dibromothiobenzamide, thiobenzamide; aromatic nitro compounds, for example nitrobenzene, m-dinitrobenzene, m-nitroaniline, m-nitrophenol, nitroanthraquinone; quinones, for example p-benzoquinone, anthraquinone, 2,3,4,5-tetramethylquinone, toluquinone, chloroanil, naphthoquinone; aromatic ketones, for example benzophenone; and mixtures of these compounds. The amount of organic compound used is generally from $10^{-5}$ to $10^{-2}$ mole, advantageously from 0.0005 to 0.001 mole, preferably from $10^{-4}$ to $10^{-3}$ mole, per mole of starting material (II).

In an advantageous embodiment of the process a light-absorbing organic compound is combined with one or more oxidizing agents.

The oxidizing agents, which are preferably inorganic, may be gaseous, solid or liquid. It is advantageous to use the following compounds: peroxo compounds, for example hydrogen peroxide, particularly in 30 to 50% by weight aqueous solution, alkali metal peroxides, hydroperoxides and peroxohydrates such as potassium hydroperoxide, lithium peroxohydrate, sodium peroxide, alkaline earth metal peroxohydrates and peroxides such as magnesium peroxide, calcium peroxide, barium peroxide, calcium peroxohydrate and magnesium peroxohydrate; hydrogen peroxide adducts such as sodium metaborate-3-hydrate-1-peroxohydrate, sodium diphosphate-3-peroxohydrate, urea peroxohydrate; peroxo acids and their salts such as sodium peroxocarbonate, peroxomonosulfuric and peroxodisulfuric acids; organic peroxides and peroxyacids such as diacetyl peroxide, benzoic peracid, dicumyl peroxide, tert.-butyl hydroperoxide, cyclohexanone peroxide; ozone; lead tetraoxide, lead tetraacetate; N-bromo-succinimide; halogen oxyacids and their salts such as sodium hypobromite, sodium chlorite, sodium chlorate, chloric acid, potassium chlorate, potassium bromate, periodic acid, sodium iodate and hypochlorous acid; chromium compounds such as chromium trioxide, potassium bichromate, ammonium bichromate, chromyl chloride; oxodizing metal salts such as ferric chloride, vanadium pentoxide chloride, ceric sulfate, mercury nitrate, potassium ferricyanide, cupric chloride, cupric sulfate and manganese tetraacetate; permanganates such as potassium permanganate; metal oxides such as cupric oxide, vanadium pentoxide, ferric oxide, manganese dioxide, molybdenum trioxide, mercuric oxide, lead dioxide, selenium dioxide, osmium tetroxide ruthenium tetroxide, argentous oxide; nitrous acid, nitro ylsulfuric acid, nitric acid and their salts, for example sodium nitrite, silver nitrate, potassium nitrate, sodium nitrate, lithium nitrate, calcium nitrate, magnesium nitrate, nickel nitrate, chromium nitrate, copper nitrate, cobalt nitrate, cerium nitrate, thorium nitrate, bismuth nitrate, iron nitrate and mercury nitrate; quinone and derivatives, for example chloranil. Appropriate mixtures of oxidizing agents or of oxidizing agents and activators, for example hydrogen peroxide and ferrous salts, ammonium molybdate, ammonium tungstate, hydrogen peroxide and osmium, vanadium and/or chromium oxides, molybdic acid and nitric acid, potassium ferricyanide and nitric acid may also be used. Oxygen or mixtures containing the same, for example air, alone or with the use of catalysts, for example the oxides of iron, chromium, aluminum, molybdenum vanadium, tungsten or zinc, with or without alkali metal oxides, and mixtures thereof; bromine or bromides; cobalt, copper, manganese, lead, cerium, mercury, or barium salts, for example the corresponding acetates, sulfates and chlorides; nickel, platinum, palladium, silver and zinc may also be used. The oxidizing agent is advantageously used in a ratio of 0.001 to 0.5 mole, preferably from 0.05 to 0.1 mole, per mole of starting material (II) and in the case when oxygen is used as the oxidizing agent in a ratio of 0.05 to 2 moles.

The oxidizing agent may also be a light-absorbing compound at the same time. The following combinations are preferred: benzoquinone and diphenylamine or m-acetaminodiphenylamine or phenothiazine or leucomethylene blue; benzoquinone and air together with diphenylamine or m-acetoaminodiphenylamine or phenothiazine or leucomethylene blue; benzophenone and air together with diphenylamine or phenothiazine; phenothiazine and air; methylene blue and air and diphenylamine. It is advantageous to use molar ratios of from 0.1 to 10 moles, preferably from 0.9 to 1.1 moles, of oxidizing agent per mole of light-absorbing compounds.

Light-absorbing compounds, oxidizing agents and polymerization inhibitors may be combined; weight ratios of from 0.5 to 50% by weight of inhibitor based on oxidizing agent are advantageous.

A substance which prevents or appreciably retards the polymerization of the monomers and thus has a stabilizing effect in relation to the monomers may be used as the polymerization inhibitor. The substance may be gaseous, solid or liquid. Those which inhibit the polymerization of vinyl compounds are preferred. It is advantageous to use the following inhibitors: thioureas, for example thiourea, methylthiourea, phenylthiourea, N,N-diphenylthiourea, N,N'-diphenylthiourea, N-methyl-N-(p-toluyl)-thiourea, S-benzyl-N-phenylisothiouronium picrate, S-methyldithiobiuret hydrochloride, phenylmethylthiourea, 2,4-dimethoxyphenylthiourea, 4-methoxyphenylthiourea, di-n-butylthiourea, 1-benzoyl-thiosemicarbazide, and dithiobiuret; phenols, thiophenols and their ethers, for example hydroquinone monomethyl ether, 4-t-butylpyrocatechol, N-benzyl-p-aminophenol, o-aminophenol; sulfur-containing heterocyclic compounds with sulfur as a substituent or in a side chain on the heterocyclic ring, for example 2-mercaptobenzimidazole, 2-mercapto-4-anilinoquinazoline and 2-thiocyanomethylbenzimidazole, or with a sulfur atom in the heterocyclic ring, for example phenothiazine, thionaphthene, 2-mercaptobenzothiazole, 2-aminobenzothiazole, 3-aminobenzoisothiazole, 2-methylbenzothiazole, diphenylene sulfide, 2,5-dimercapto-1,3,4-thiadiazole and tetramethylene-trithione; substituted aromatic amines, for example N-phenyl-$\alpha$-naphthylamine and N-phenyl-$\beta$-naphthylamine; nitroso compounds, for example o-nitrosophenol, m-nitrosophenol, p-nitrosophenol, N-nitrosophenylhydroxylammonium salt (cupferron), nitrogen monoxide and dinitrogen tetroxide; organic phosphorus compounds, for example triphenyl phosphine and triphenyl phosphite; thiocarboxamides, for example thioacetamide, anthranilic thiamide, 2-amino-5-nitrothiobenzamide, 2-amino-3-bromo-5-nitrothiobenzamide, 2-amino-3,5-dibromothiobenzamide, thiobenzamide; and corresponding mixtures. Generally from $10^{-5}$ to $10^{-2}$, preferably from $10^{-4}$ to $10^{-3}$, mole of polymerization inhibitor is used per mole of starting material (II). For example molybdic acid and phenothiazine or phenylthiourea; nitric acid and phenylthiourea, potassium ferricyanide and thiourea; chromium trioxide and thionaphthene; hydrogen peroxide and N-phenyl-$\alpha$-naphthylamine; potassium nitrate and N-phenyl-$\beta$-naphthylamine or dithiobiuret may be used together. Similarly oxidizing agents may be used which may at the same time serve as polymerization inhibitors, for example nitrogen monoxide, dinitrogen tetroxide and potassium nitrosodisulfonate.

The reaction may be carried out at atmospheric or superatmospheric pressure, continuously or batchwise, generally at a temperature of from +40° to +200°C, preferably from +50° to +150°C. Organic solvents which are inert under the reaction conditions, for example aliphatic hydrocarbons such as n-pentane, n-heptane, cycloaliphatic hydrocarbons such as cyclohexane, or mixtures of the same, may be used if desired.

The reaction may be carried out as follows: Any apparatus in which the styrene can be contacted intimately with the catalyst may be used, in the case of a liquid catalyst such as the said acids for example a packed tower, a bubbler, a cascade reactor, sieve plate column, Oldershaw column, glass plate column, bubble cap tray column or valve tray column. Gaseous or liquid styrene is dimerized cocurrently or countercurrently with the acid in the reactor at the reaction temperature. In accordance with the type of reactor, the acid, and if desired the oxidizing agent and inhibitor may be placed therein and the styrene passed therethrough while mixing well. When a column is used the acid is advantageously passed continuously through the reactor, the throughput of liquid advantageously being from 10 to 100 m³ per m² of column cross-section per hour. After the acid has left the reactor it may be separated from the organic reaction product and returned to the reactor. The vapor speed of the gaseous styrene is advantageously from 0.1 to 2.0 meters per second based on the cross-section of the column. The residence time in the reactor is as a rule from 0.1 to 5 minutes. The reaction mixture is then separated from the acid in a separating plant downstream of the reactor and the end product is isolated by a conventional method, for example by fractional distillation. Unreacted starting material and the acid are returned to the reaction. The starting material is generally supplied to the reactor in gaseous or liquid condition. It is also possible to supply it in the liquid state, to vaporize it within the reactor and only then to contact it with the acid and so begin the reaction.

A mixture of starting material (II) and with or without oxidizing agent and inhibitor may be reacted continuously or batchwise in a stirred vessel or a cascade of stirred vessels at the reaction temperature for 30 minutes to 2 hours. In this case it is convenient to use a temperature of from 30°C to the boiling point of the styrene concerned at the reaction pressure, for example 0.3 to 3.0 atmospheres.

The following is also an advantageous embodiment of the reaction; the styrene (II) is dimerized at the reaction temperature in the presence of an acid and if desired the appropriate oxidizing agent and an inhibitor in the specified concentrations in a stirred vessel or in a stirred cascade with intense mixing, advantageously with a stirring energy of from 3 to 8 kw/m$^3$. The residence time of the reaction mixture in the reaction chamber is generally from 20 minutes to 2 hours. At the beginning the mixture of the reactants may be prepared at the reaction temperature or at a lower temperature and then brought to the reaction temperature. The individual stirred vessels in a cascade of the same may be kept at different reaction temperatures.

The portion of the reaction mixture which is continuously withdrawn is subjected to phase separation. The separated aqueous phase, which contains the acid, may be reused immediately for the reaction. The acid may however be processed in a conventional manner, for example by filtration, centrifuging, distillation or extraction. Each of the vessels in the cascade of stirred vessels may be supplied by way of its own acid circulation system or all the vessels may be supplied by way of a common circulation system. In the former case the concentration of the acid, for example, may be varied from vessel to vessel. The end product is isolated by a conventional method, for example by distillation, from the organic phase.

In the case of solid catalysts the starting materials (II) may be passed in liquid or gaseous condition at the reaction temperature continuously over a bed of catalyst in a tubular reactor. In batchwise operation, mixtures of starting material (II) and solid catalyst may be reacted in a similar way as in the case of liquid acid catalysts. The catalyst may be suspended in the liquid starting material (II) or fluidized (fluidized bed).

The oxidizing agent and the polymerization inhibitor may be supplied to the reaction in any suitable way, for example mixed with the starting material (II), the solid catalyst, or in solution or suspension in the liquid catalyst or as a separate addition. In the separation of the end product, they may be separated from the organic phase, depending on their constitution, and reused or in the case of an acid-soluble oxidizing agent may be supplied to the reaction again together with the acid.

The exposure to light (photoactivation) of the light-absorbing compounds may be carried out during the dimerization of the styrene, for example by directing light into the reaction vessel, or prior to the reaction for example by irradiating the photoactivatable substance while undissolved or advantageously in solution. In a particularly simple and economic embodiment the solvent used for such solutions is the styrene intended for the dimerization or the catalyst, for example phosphoric acid.

Light sources which emit light of from 2000 to 8000 A, preferably from 2500 to 4500 A, are suitable for the photoactivation. Efficient utilization of the light energy is achieved when the main emission of the light source falls within the absorption bands of the organic compounds being used. In the light activation of compounds during the reaction or in the exposure of the compounds prior to the reaction using a styrene as solvent it is advisable to eliminate wavelengths below 2900 A by means of a glass filter. The light source may be sunlight or artificial light, for example of tungsten lamps, xenon lamps, mercury vapor discharge lamps, graphite arcs, carbon arcs, fluorescent lamps. Irradiation is conveniently carried out from 0.2 to 10,000 watt hours, preferably from 2 to 1000 watt hours, and particularly from 10 to 200 watt hours of light per kilogram of starting material (II). The light source may be introduced into the reaction zone, for example in the form of a submerged lamp. The light-absorbing organic compound may be advantageously irradiated in a continuous flow reactor or, in the case of batchwise operation, in individual batches. When continuous or batchwise irradiation is carried out during the reaction it is convenient to begin and end the irradiation at the same time as the reaction begins and ends. In batchwise operation the irradiation may also be broken off before the dimerization ends. In the case of separate irradiation appropriate irradiation periods are for example from five minutes to two hours. In the case of simultaneous irradiation the reaction may be carried out continuously or batchwise at atmospheric or superatmospheric pressure, generally at a temperature of from +40° to +200°C, preferably from +50° to +150°C. If irradiation of the organic compound or a solution of the same for example in one of the abovementioned solvents is carried out prior to the reaction, advantageous irradiation temperatures are from 15° to 35°C. The separate continuous or batchwise irradiation of the organic compound, with or without an oxidizing agent, polymerization inhibitor, solvent and/or catalyst, may also be carried out shortly prior to entry into the reaction zone; for example the photoactivatable substance dissolved in the styrene supplied to the reaction may flow past an irradiating lamp before entering the reaction zone.

The compound activated by light before or during the reaction may be supplied in any suitable way to the reaction, for example mixed with the starting material (II), the solid catalyst and/or optionally the oxidizing agent or inhibitor or in solution or suspension in the liquid catalyst or as a separate addition. In the separation of the end product, the catalyst, depending on its constitution, may be separated from the organic phase and used again or, in the case of an oxidizing agent which is soluble in acid, may be returned to the reaction.

The compounds which can be prepared by the process of the invention are valuable starting materials for the production of dyes and pest control agents. In this connection reference is made to the abovementioned publications and to U.S. Pat. Nos. 3,658,893 and 3,655,741.

The following Examples illustrate the invention. The parts indicated in the Examples are by weight and bear the same relation to parts by volume as the kilogram to the liter.

EXAMPLES 1 to 12

Batchwise liquid-liquid dimerization:

Method A: 100 parts by volume of phosphoric acid (98% by weight) at 25°C is placed in a stirred vessel and a light-absorbing organic compound as set out in the following Table 1 is added to it. The mixture is irradiated for 10 minutes with a mercury vapor lamp (15 watt hours per kilogram of styrene) while passing 2000 parts of air therethrough. Then while stirring at 60°C 104 parts of styrene is added to the irradiated solution within 40 minutes. The organic phase is distilled. The composition of the distillate is determined chromatographically. The total yield of dimers (D), the yield of linear styrene dimers (S) and the yield of end product (EP) is given for the various compounds in the following Table 1. The yield of D and EP is given in % of theory based on starting material (II) and the yield of S is given in % by weight based on D.

Method B: The amount of organic compound in parts indicated in the Table 1 is added to 104 parts by weight of styrene and irradiated analogously to Method A while passing air through. The irradiated solution is then added at 60°C while stirring to 100 parts by volume of phosphoric acid (99% by weight) within 40 minutes and the mixture is worked up analogously to method A. Example 1 is a comparative Example and is carried out by Method A or B. In the Table Ex = Example No. and MT = Method.

TABLE 1

| Ex | Additive | Parts | MT | D | S | EP |
|----|----------|-------|-----|----|----|----|
| 1 | — | — | A/B | 66 | 10 | 60 |
| 2 | phenothiazine | 0.5 | A | 86 | 10 | 77 |
| 3 | phenothiazine | 0.5 | B | 86 | 9 | 78 |
| 4 | nitrobenzene | 0.5 | B | 86 | 10 | 77 |
| 5 | leucomethylene blue | 0.5 | A | 87 | 8 | 80 |
| 6 | hydrazobenzene | 0.5 | A | 84 | 8 | 77 |
| 7 | phenylthiourea | 0.5 | A | 86 | 10 | 77 |
| 8 | thianthrene | 0.5 | A | 85 | 8 | 78 |
| 9 | diphenylamine | 0.5 | A | 84 | 6 | 79 |
| 10 | phenothiazine<br>p-benzoquinone | 0.5<br>0.25 | A | 88 | 12 | 77 |
| 11 | diphenylamine<br>p-benzoquinone | 0.42<br>0.25 | A | 92 | 10 | 83 |
| 12 | N-phenyl-β-naphthylamine | 0.5 | A | 86 | 10 | 77 |

EXAMPLE 13

100 parts by volume of phosphoric acid (98% by weight) and 0.5 part of nitrobenzene are heated to 80°C in a stirred vessel fitted with a submerged mercury vapor lamp (50 watt hours per kilogram of styrene). At this temperature 104 parts of styrene is added in portions over 40 minutes while irradiating the mixture. The organic phase is then separated and distilled. A total yield of 86% of the dimer mixture (D) is obtained which contains 9% of linear styrene dimers (S). The yield of end product (I) is 78%.

EXAMPLES 14-16

Continuous dimerization:

55 parts of styrene with a dissolved amount as given in parts in the following Table 2 of an organic compound (a) and of an organic compound (b) is metered into a photoreactor having a submerged ultraviolet lamp fitted inside it. The residence time in the photoreactor is 20 minutes at a temperature of 25°C and 300 parts by volume of air is passed in. The light energy with which the styrene supplied is irradiated is 10 watt hours per kilogram.

The styrene is further passed into a continuously stirred apparatus in which there is 100 parts of phosphoric acid (98%) and 55 parts of methylphenylindane. The reaction temperature is 70°C. 155 parts per hour of the two-phase reaction mixture of 55 parts of organic phase and 100 parts of phosphoric acid is fed through a lateral outlet into a separator kept at 130°C to 140°C. The acid which separates as the lower phase is returned to the reactor. The organic phase is distilled and analyzed by gas chromatography.

TABLE 2

| Example | 14 | 15 | 16 |
|---------|-----|-----|-----|
| Addition (a) parts per 55 parts of styrene | p-benzoquinone<br>0.06 | phenothiazine<br>0.06 | phenothiazine<br>0.06 |
| Addition (b) parts per 55 parts of styrene | diphenylamine<br>0.1 | —<br>— | p-benzoquinone<br>0.06 |
| Dimers (D) | 89.0 | 87.5 | 87.1 |
| Linear dimers (S) | 8.1 | 6.0 | 6.1 |
| Yield of end product I in % of theory | 81.8 | 82.2 | 81.8 |

We claim:

1. A process for the production of a 1-methyl-3-phenylindane of the formula (I):

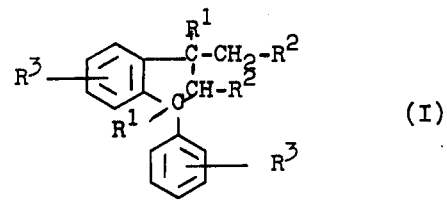

(I)

in which
R¹ is alkyl or hydrogen;
R² is alkyl or hydrogen; and
R³ is alkyl, hydrogen or halogen
by dimerization of styrene in the presence of a catalyst wherein the reaction is carried out with a styrene of the formula (II):

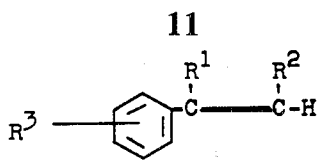

in which $R^1$, $R^2$ and $R^3$ have the above meanings, in the presence or absence of an oxidizing agent and in the presence of an organic compound capable of absorbing light of from 2000 to 8000 Å and irradiated with said light.

2. A process as claimed in claim 1 carried out in the presence of a silicic acid compound, phosphoric acid, sulfuric acid or a haloalkanoic acid.

3. A process as claimed in claim 1 carried out in the presence of a gaseous starting material (II) and in a ratio of from 50 to 1000 moles of acid (calculated as 100%) per mole of starting material (II).

4. A process as claimed in claim 1 carried out in the presence of a liquid starting material (II) and in a ratio of from 4 to 0.25 part by volume of acid (calculated as 100%) per part by volume of starting material (II).

5. A process as claimed in claim 1, carried out with acid in a ratio by weight of from 70 to 95% of phosphoric acid (calculated as 100%), from 0 to 20% of sulphuric acid (calculated as 100%) and from 0 to 20% of water.

6. A process as claimed in claim 1, carried out with an oxidizing agent in a ratio of from 0.001 to 0.5 mole per mole of starting material (II).

7. A process as claimed in claim 1, carried out with the light-absorbent organic compound in a ratio of from $10^{-5}$ to $10^{-2}$ mole per mole of starting material (II).

8. A process as claimed in claim 1, wherein the organic compound is irradiated with from 0.2 to 10,000 watt hours of light per kilogram of the starting material (II).

9. A process as claimed in claim 1, carried out in the presence of from $10^{-5}$ to $10^{-2}$ mole of a polymerization inhibitor per mole of starting material (II).

10. A process as claimed in claim 1 carried out in the presence of a polymerization inhibitor in a ratio by weight of from 0.5 to 50% based on oxidizing agent.

11. A process as claimed in claim 1 carried out at a temperature of from 40° to 200°C.

12. A process as claimed in claim 1 carried out at a temperature of from 50° to 150°C.

13. A process as claimed in claim 1 carried out in the presence of a solvent which is inert under the reaction conditions.

* * * * *